United States Patent
Somers

Patent Number: 6,121,319
Date of Patent: *Sep. 19, 2000

[54] MONOESTERS OF PROBUCOL FOR THE TREATMENT OF CARDIOVASCULAR AND INFLAMMATORY DISEASE

[75] Inventor: Patricia K. Somers, Atlanta, Ga.

[73] Assignee: AtheroGenics, Inc., Alpharetta, Ga.

[*] Notice: This patent is subject to a terminal disclaimer.

[21] Appl. No.: 09/078,935

[22] Filed: May 14, 1998

Related U.S. Application Data

[60] Provisional application No. 60/047,020, May 14, 1997.

[51] Int. Cl.⁷ .......................... A01N 37/02; A61K 31/10; A61K 31/225

[52] U.S. Cl. .......................... 514/548; 514/712; 514/824; 514/825; 514/826; 514/855

[58] Field of Search .................................... 514/548, 712, 514/824, 855, 826, 825

[56] References Cited

U.S. PATENT DOCUMENTS

| | | |
|---|---|---|
| 3,179,701 | 4/1965 | Rocklin . |
| 3,479,407 | 11/1969 | Laufer . |
| 3,576,883 | 4/1971 | Neuworth . |
| 3,952,064 | 4/1976 | Whalley . |
| 4,029,812 | 6/1977 | Wagner . |
| 4,076,841 | 2/1978 | Wagner . |
| 4,078,084 | 3/1978 | Wagner . |
| 4,115,590 | 9/1978 | Lerner . |
| 4,752,616 | 6/1988 | Hall . |
| 4,755,524 | 7/1988 | Mueller . |
| 4,954,514 | 9/1990 | Kita . |
| 5,155,250 | 10/1992 | Parker . |
| 5,206,247 | 4/1993 | Regnier . |
| 5,262,439 | 11/1993 | Parthasarathy . |
| 5,380,747 | 1/1995 | Medford . |
| 5,608,095 | 3/1997 | Parker . |
| 5,627,205 | 5/1997 | Regnier . |
| 5,750,351 | 5/1998 | Medford . |
| 5,773,209 | 6/1998 | Medford et al. . |
| 5,773,231 | 6/1998 | Medford et al. . |
| 5,783,596 | 7/1998 | Medford et al. . |
| 5,792,787 | 8/1998 | Medford et al. . |
| 5,807,884 | 9/1998 | Medford et al. . |
| 5,811,449 | 9/1998 | Medford et al. . |
| 5,821,260 | 10/1998 | Medford et al. . |
| 5,846,959 | 12/1998 | Medford et al. . |

FOREIGN PATENT DOCUMENTS

| | | |
|---|---|---|
| 190 682 | 8/1986 | European Pat. Off. . |
| 0 348 203 A1 | of 1989 | European Pat. Off. . |
| 317 165 | 5/1989 | European Pat. Off. . |
| 0 405 788 A2 | 1/1991 | European Pat. Off. . |
| 621 255 | 10/1994 | European Pat. Off. . |
| 0 763 527 A1 | 3/1997 | European Pat. Off. . |
| 2130975 | 11/1972 | France . |
| 2133024 | 11/1972 | France . |
| 2134810 | 12/1972 | France . |
| 2140769 | 1/1973 | France . |
| 2140771 | 1/1973 | France . |
| 2168137 | 8/1973 | France . |
| 1 136 539 | 12/1968 | United Kingdom . |
| 1 148 550 | 4/1969 | United Kingdom . |
| WO 95/15760 | 6/1995 | WIPO . |
| WO 95/30415 | 11/1995 | WIPO . |
| WO 96 12703 | 5/1996 | WIPO . |
| WO 97/15546 | 5/1997 | WIPO . |
| WO 98 22418 | 5/1998 | WIPO . |
| WO 98/51662 | 11/1998 | WIPO . |

OTHER PUBLICATIONS

Baron, J.L. et al., J. Clin. Invest. 93, 1700–1708 (1994).
Brown and Goldstein, Ann. Rev. Biochem. 52, 223 (1983).

(List continued on next page.)

*Primary Examiner*—Gary L. Kunz
*Assistant Examiner*—Everett White
*Attorney, Agent, or Firm*—Sherry M. Knowles; Jacqueline Haley; King & Spalding

[57] ABSTRACT

This invention is a method and composition for the inhibition of VCAM-1, and in particular for the treatment of cardiovascular or inflammatory disease, including atherosclerosis, that includes the administration of an effective amount of an ester of probucol.

14 Claims, 8 Drawing Sheets

OTHER PUBLICATIONS

Burkly, L.C. et al., Diabetes 43, 523–534 (1994).
Carew et al. Proc. Natl. Acad. Sci. U.S.A. 84:7725–7729 (1987).
Folkman, J. and Shing, Y., Biol. Chem. 10931–10934 (1992).
Heeg et al., Plasma Levels of Probucol in Man After Single and Repeated Oral Doses, *La Nouvelle Presse Medicale*, 9(40) (1980).
Kazuya et al. J. Lipid Res. 32; 197–204 (1991).
Koch, A.E. et al. Lab. Invest. 64, 313–322 (1991).
Miller, Ann. Rev. Med. 31,97 (1980).
Morales–Ducret, J. et al., Immunol. 149, 1421–1431 (1992).
Ohkawara, Y., et al., Am. j. Respir. Cell Mol. Biol. 12,4–12 (1995).
Oroez, C.G. et al., Immunol. Lett. 32, 7–12 (1992).
Parthasarathy, S. et al., Probucol Inhibits Oxifative Modification of Low Density Lipoprotein, *J. Clin. Invest.,* 77 641–644 (1986).
Patton et al., Clin. Chem. 29, 1980 (1983).
Chemical Abstracts 127:75973, 1996.
Chemical Abstracts 82:86190, 1975.
Chemical Abstracts 126:277465, 1997.
Chemical Abstracts 94:30290, 1980.
Chemical Abstracts 86:5066, 1977.
Chemical Abstracts 122:187387, 1995.
Chemical Abstracts 124:8690, 1996.
Chemical Abstracts 124:146082, 1995.
Chemical Abstracts 110:212254, 1989.

MONOESTERS OF PROBUCOL FOR THE TREATMENT OF CARDIOVASCULAR AND INFLAMMATORY DISEASE

This application claims priority to U.S. provisional application No. 60/047,020 filed on May 14, 1997.

This invention is a method and composition for the inhibition of VCAM-1, and in particular for the treatment of cardiovascular or inflammatory disease, including atherosclerosis, that includes the administration of an effective amount of an ester of probucol.

BACKGROUND OF THE INVENTION

Cardiovascular disease is currently the leading cause of death in the United States. Approximately ninety percent of cardiovascular disease is presently diagnosed as atherosclerosis. Cardiovascular disease has been linked to several causative factors, which include hypercholesterolemia, hyperlipidemia, and the expression of VCAM-1 in vascular endothelial cells.

Hypercholesterolemia and Hyperlipidemia

Hypercholesterolemia is an important risk factor associated with cardiovascular disease. Serum lipoproteins are the carriers for lipids in the circulation. Lipoproteins are classified according to their density: chylomicrons, very low-density lipoproteins (VLDL), low density lipoproteins (LDL) and high-density lipoproteins (HDL). Chylomicrons primarily participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulate endogenous cholesterol levels in those tissues. HDL transports cholesterol from peripheral tissues to the liver. Arterial wall cholesterol is derived almost exclusively from LDL. Brown and Goldstein, *Ann. Rev. Biochem.* 52, 223 (1983); Miller, *Ann. Rev. Med.* 31, 97 (1980)). In patients with low levels of LDL, the development of atherosclerosis is rare.

Elevated cholesterol levels are associated with a number of disease states, including restenosis, angina, cerebral atherosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

If it has been determined that hypercholesterolemia is due to elevated LDL (hyperlipidemia), the lowering of LDL levels by dietary therapy is attempted. There are several drug classes that are commonly used to lower LDL levels, including bile acid sequestrants, nicotinic acid (niacin), and 3-hydroxy-3-methylglutaryl coenzyme A (HMG CoA) reductase inhibitors. Probucol and the fibrate derivatives are sometimes used as adjunctive therapy, usually in combination with other medications. The HMG CoA reductase inhibitors have been termed statins or vastatins. Statins are among the most effective agents currently on the market for hypercholesterolemia, and include pravastatin (Pravchol, Bristol Myers Squibb), atrovastatin (Warner Lambert/Pfizer), simvastatin (Zocor, Merck), lovastatin (Mevacor, Merck), and fluvastatin (Lescol).

For many patients, diet plus one of the hypolipidemic agents will be sufficient. However, for patients with an initial LDL cholesterol level of greater than 200 mg/dl, therapy needs to lower LDL levels by 50% or more. Although a single agent may occassionally achieve this degree of LDL lowering, it is far more common to see decreases of only 20 to 30%. Thus, for the patient with heterozygous familial hypercholesterolemia with an LDL cholesterol of 200 to 400 mg/dl, a combination of two, or occasionally, three hypolipidemic drugs will be required to achieve an LDL cholesterol level of less than 100 mg/ml. Combinations of a bile sequestrant resin and nicotinic acid can lower LDL levels by 45% to 55%, a resin plus a statin, by about 50% to 60%, nicotinic acid plus a statin by about 50%, and triple drug therapy, using a combination of a bile acid-binding resin, a statin, and nicotinic acid, by as much as 70%.

Evidence suggests that the atherogenic effects of low density lipoprotein (LDL) may be in part mediated through its oxidative modification. Probucol has been shown to possess potent antioxidant properties and to block oxidative modification of LDL. Consistent with these findings, probucol has been shown to actually slow the progression of atherosclerosis in LDL receptor-deficient rabbits as discussed in Carew et al. Proc. *Natl. Acad. Sci. U.S.A.* 84:7725–7729 (1987). Most likely, probucol is effective because it is highly lipid soluble and is transported by lipoproteins, thus protecting them against oxidative damage.

Probucol is chemically related to the widely used food additives 2,[3]-tert-butyl-4-hydroxyanisole (BHA) and 2,6-di-tert-butyl-4-methyl phenol (BHT). Its fill chemical name is 4,4'-(isopropylidenedithio) bis(2,6-di-tert-butylphenol).

Today, probucol is used primarily to lower serum cholesterol levels in hypercholesterolemic patients. Probucol is commonly administered in the form of tablets available under the trademark Lorelco™. Unfortunately, probucol is almost insoluble in water and therefore cannot be injected intravenously. In fact, probucol is difficult for cells to absorb in vitro because of its poor miscibility in buffers and media for cell culture. Solid probucol is poorly absorbed into the blood, and is excreted in substantially unchanged form. Further, the tablet form of probucol is absorbed at significantly different rates and in different amounts by different patients. In one study (Heeg et al., *Plasma Levels of Probucol in Man After Single and Repeated Oral Doses*, La Nouvelle Presse Medicale, 9:2990–2994 (1980)), peak levels of probucol in sera were found to differ by as much as a factor of 20 from patient to patient. In another study, Kazuya et al. J. Lipid Res. 32; 197–204 (1991) observed an incorporation of less than about 1 $\mu$g of probucol/$10^6$ cells when endothelial cells are incubated for 24 h with 50 $\mu$M probucol.

U.S. Pat. No. 5,262,439 to Parthasarathy discloses soluble analogs of probucol in which one or both of the hydroxyl groups are replaced with ester groups that impart water solubility to the compound. In one embodiment, the soluble derivative is selected from the group consisting of a mono- or di-succinic acid ester, glutaric acid ester, adipic acid ester, suberic acid ester, sebacic acid ester, azelaic acid, or maleic acid ester of probucol. In another embodiment, the probucol derivative is a mono- or di-ester in which the ester contains an alkyl or alkenyl group that contains a functionality selected from the group consisting of a carboxylic acid group, amine group, salt of an amine group, amide groups, amide groups, and aldehyde groups.

A series of French patents disclose that certain probucol derivatives are hypocholesterolemic and hypolipemic agents: Fr 2168137 (bis 4-hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-alkyl-5-t-alkyl-4-thiazole-5-carboxy) phenylthio)alkanes; FR 2133024 (bis-(4-nicoinoyloxyphenythio)propanes; and Fr 2130975 (bis(4-(phenoxyalkanoyloxy)phenylthio)alkanes).

U.S. Pat. No. 5,155,250 discloses that 2,6-dialkyl-4-silylphenols are antiatheroscierotic agents. The same compounds are disclosed as serum cholesterol lowering agents in PCT Publication No. WO 95/15760, published on Jun. 15, 1995. U.S. Pat. No. 5,608,095 discloses that alkylated-4-silyl-phenols inhibit the peroxidation of LDL, lower plasma cholesterol, and inhibit the expression of VCAM-1, and thus are useful in the treatment of atherosclerosis.

Expression of VCAM-1

Adhesion of leukocytes to the endothelium represents a fundamental, early event in cardiovascular disease as well as in a wide variety of inflammatory conditions, including autoimmune disorders and bacterial and viral infections. Leukocyte recruitment to the endothelium is started when inducible adhesion molecule receptors on the surface of endothelial cells interact with counterreceptors on immune cells. Vascular endothelial cells determine which type of leukocytes (monocytes, lymphocytes, or neutrophils) are recruited, by selectively expressing specific adhesion molecules, such as vascular cell adhesion molecule-1 (VCAM-1), intercellular adhesion molecule-1 (ICAM-1), and E-selectin (ELAM). In the earliest stage of the atherosclerotic lesion, there is a localized endothelial expression of VCAM-1 and selective recruitment of mononuclear leukocytes that express the integrin counterreceptor VLA-4. Because of the selective expression of VLA-4 on monocytes and lymphocytes, but not neutrophils, VCAM-1 is important in mediating the selective adhesion of mononuclear leukocytes. VCAM-1 is involved as a mediator in chronic inflammatory disorders such as asthma, rheumatoid arthritis and autoimmune diabetes. For example, it is known that the expression of VCAM-1 and ICAM-1 are increased in asthmatics. Pilewski, J. M., et al. *Am. J Respir. Cell Mol. Biol.* 12, 1–3 (1995); Ohkawara, Y., et al., *Am. J Respir. Cell Mol Biol.* 12, 4–12 (1995). Additionally, blocking the integrin receptors for VCAM-1 and ICAM-1 (VLA-4 and LFA-1, respectfully) suppressed both early and late phase responses in an ovalbumin-sensitized rat model of allergic airway responses. Rabb, 11. A., et al.,*Am. J. Respir. Care Med.* 149, 1186–1191 (1994). There is also increased expression of endothelial adhesion molecules, including VCAM-1, in the microvasculature of rheumatoid synovium. Koch, A. E. et al., *Lab. Invest.* 64, 313–322 (1991); Morales-Ducret, J. et al., *Immunol.* 149, 1421–1431 (1992). Neutralizing antibodies directed against VCAM-1 or its counter receptor, VI A-4, can delay the onset of diabetes in a mouse model (NOD mice) which spontaneously develop the disease. Yang, X. D. et al., *Proc. Natl. Acad. Sci. U.S.A.* 90, 10494–10498 (1993); Burkly, L. C. et al., *Diabetes* 43, 523–534 (1994); Baron, J. L. et al., *J. Clin. Invest.* 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Oroez, C. G. et al., *Immunol. Lett.* 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. F. et al., *Nature* 376, 517–519 (1995). Inhibitors of the expression of soluble VCAM-1 have potential therapeutic value in treating diseases with a strong angiogenic component, including tumor growth and metastasis. Folkman, J., and Shing, Y., *Biol. Chem.* 10931–10934 (1992).

VCAM-1 is expressed in cultured human vascular endothelial cells after activation by lipopolysaccharide (LPS) and cytokines such as interleukin-1 (IL-1) and tumor necrosis factor (TNF-a). These factors are not selective for activation of cell adhesion molecule expression.

Subsequent conversion of leucocytes to foamy macrophages results in the synthesis of a wide variety of inflammatory cytokines, growth factors, and chemoattractants that help propagate the leukocyte and platelet recruitment, smooth muscle cell proliferation, endothelial cell activation, and extracellular matrix synthesis characteristic of maturing atherosclerotic plaque.

Molecular analysis of the regulatory elements on the human VCAM-1 gene that control its expression suggests an important role for nuclear factor-kB (NF-kB), a transcriptional regulatory factor, or an NF-kB like binding protein in oxidation-reduction-sensitive regulation of VCAM-1 gene expression. Transcriptional factors are proteins that activate (or repress) gene expression within the cell nucleus by binding to specific DNA sequences called "enhancer elements" that are generally near the region of the gene, called the "promoter," from which RNA synthesis is initiated.

The promoters for both VCAM-1 and ICAM-1 have been cloned and characterized. For example, both promoters contain multiple DNA sequence elements which can bind the transcription factor, NF-kB. Iademarco, M. F. et al., *J Biol. Chem.* 267, 16323–16329 (1992).

Nuclear factor-kB is a ubiquitously expressed multisubunit transcription factor activated in several cell types by a large and diverse group of inflammatory agents such as TNFa, IL-1B, bacterial endotoxin, and RNA viruses. It plays a key role in mediating inflammatory and other stress signals to the nuclear regulatory apparatus. Although the precise biochemical signals that activate NF-kB are unknown, this transcriptional factor may integrate into a common molecular pathway many of the risk factors and "causative" signals of atherosclerosis, such as hyperlipidemia, smoking, hypertension, and diabetes mellitus.

The activation of NF-kB in vascular endothelial cells by diverse signals can be specifically inhibited by antioxidants such as N-acetylcysteine and pyrrolidine dithiocarbamate. This has led to the hypothesis that oxygen radicals play an important role in the activation of NF-kB through an undefined oxidation-reduction mechanism. Because an NF-kB-like enhancer element also regulates the transcription of the VCAM-1 promoter in an oxidation-reduction-sensitive manner, it was hypothesized that oxidative stress in the atherosclerotic lesion may play a role in regulating VCAM-1 gene expression through this oxidation-reduction-sensitive transcriptional regulatory protein. U.S. Pat. No. 5,380,747 (PCT/US93/10496) disclosed for the first time that the expression of VCAM-1 in vascular endothelial cells can be inhibited by the administration of a class of dithiocarbamates, which include pyrrolidine dithiocarbamate. These dithiocarbamates are thus useful in the treatment of cardiovascular disease, and have now been shown to significantly reduce the presence of atherosclerotic lesions in hypercholesterolemic rabbits.

It has been hypothesized that modification of low-density lipoprotein (LDL) into oxidatively modified LDL (ox-LDL) by reactive oxygen species is the central event that initiates and propagates atherosclerosis. Steinberg, et al., N. Engl. J. Med. 1989; 320:915–924. Oxidized LDL is a complex structure consisting of at least several chemically distinct oxidized materials, each of which, alone or in combination, may modulate cytokine-activated adhesion molecule gene expression. Fatty acid hydroperoxides such as linoleyl hydroperoxide (13-HPODE) are produced from free fatty acids by lipoxygenases and are an important component of oxidized LDL.

It has been proposed that a generation of oxidized lipids is formed by the action of the cell lipoxygenase system and that the oxidized lipids are subsequently transferred to LDL. There is thereafter a propagation reaction within the LDL in the medium catalyzed by transition metals and/or sulfhydryl compounds. Previous investigations have demonstrated that fatty acid modification of cultured endothelial cells can alter their susceptibility to oxidant injury. PCT/US95/05880 disclosed that polyunsaturated fatty acids and their hydroperoxides induce the expression of VCAM-1, but not ICAM-1 or E-selectin in human aortic endothelial cells, through a mechanism that is not mediated by cytokines or other noncytokine signals. This was a fundamental discovery of an important and previously unknown biological pathway in VCAM-1 mediated immune responses. It was also reported in PCT/US95/05880 that the induction of VCAM-1 by polyunsaturated fatty acids and their hydroperoxides is supressed by dithiocarbamates, including pyrrolidine dithiocarbamate.

Given that cardiovascular disease is currently the leading cause of death in the United States, there is a need to provide new therapies for its treatment. It is a goal to provide new agents that can simultaneously treat hypercholesterolemia, hyperlipidemia, and can inhibit the expression of VCAM-1 in vascular endothelial cells.

Therefore, it is an object of the present invention to provide a method and composition for suppression of VCAM-1, and in particular a method for the treatment of cardiovascular disease.

It is a further object of the present invention to provide a method and composition for the treatment of cardiovascular disease that can simultaneously treat hypercholesterolemia, hyperlipidemia, and can inhibit the expression of VCAM-1 in vascular endothelial cells.

SUMMARY

It has been discovered that monoesters of probucol are effective in simultaneously reducing cholesterol, lowering LDL, and inhibiting the expression of VCAM-1, and thus these compounds are useful as composite cardiovascular agents. Since the compound exhibits three important vascular protecting activities simultaneously, the patient can take one drug instead of multiple drugs to achieve the same effect. This should increase consistency of therapy and patient compliance.

It was surprising to learn that the monoester of probucol inhibits VCAM-1 given that probucol itself, while a potent antioxidant, does not significantly affect VCAM-1 expression. Diesters of probucol also do not significantly affect VCAM-1 expression, nor do statins.

It has also been discovered that the monosuccinic acid ester of probucol reduces HDL only to a small extent in rabbits and does not affect HDL in mice and monkeys. Probucol, in contrast, reduces LDL only to a small extent and reduces HDL significantly. Statins reduce LDL and may or may not effect HDL.

It has further been discovered that monoesters of probucol, and in particular, the monosucccinic acid ester of probucol (referred to herein as "MSE"), selectively inhibits TNF-induced VCAM-1 and MCP-1 gene expression but not ICAM-1 in human aortic endothelial cells. MSE does not affect NF-kB activation. MSE is used herein as illustrative of monoesters of probucol. The use of MSE as an illustration is for convenience of discussion only and is not meant to limit the scope of the invention.

Given the discovery that monoesters of probucol, and in particular, the monosuccinic acid ester of probucol, block the induced expression of the endothelial cell surface adhesion molecule VCAM-1, they are useful in the treatment of any disease that is mediated by VCAM-1, including atherosclerosis, post-angioplasty restenosis, coronary artery diseases, angina, and other cardiovascular diseases, as well as noncardiovascular inflammatory diseases that are mediated by VCAM-1. The compounds can also be used in the treatment of cardiac transplant rejections.

The compounds described herein are useful in both the primary and adjunctive medical treatment of cardiovascular disease. The compounds are used in primary treatment of, for example, coronary disease states including atherosclerosis, post-angioplasty restenosis, coronary artery diseases, and angina. The compounds can be administered to treat small vessel disease that is not treatable by surgery or angioplasty, or other vessel disease in which surgery is not an option. The compounds can also be used to stabilize patients prior to revascularization therapy.

The invention described herein when used appropriately, provides the possibility to medically "cure" atherosclerosis by preventing new lesions from developing and causing established lesions to regress.

In an alternative embodiment, the compounds disclosed herein can be used in the treatment of inflammatory skin diseases that are mediated by VCAM-1, and in particular, human endothelial disorders that are mediated by VCAM-1, which include, but are not limited to, asthma, psoriasis, eczematous dermatitis, Kaposi's sarcoma, multiple sclerosis, as well as proliferative disorders of smooth muscle cells.

In yet another embodiment, the compounds disclosed herein can be selected to treat antiinflammatory conditions that are mediated by mononuclear leucocytes.

DETAILED DESCRIPTION OF THE INVENTION

I. Definitions

Figure 1:
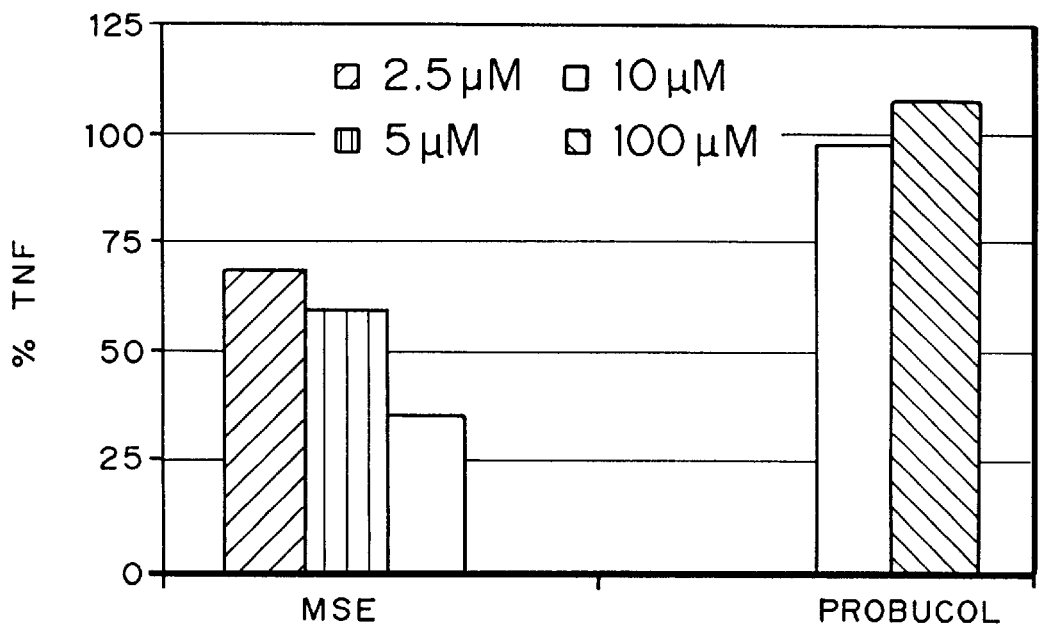
FIG. 1 is a bar chart graph of the comparison of the effect of the monosuccinic acid ester of probucol with probucol at 2.5 $\mu$M, 5 $\mu$M, 10 $\mu$M and 100 $\mu$M on VCAM-1 expression in HAEC cells.

The term "monoester of probucol," as used herein, includes (i) any monoester of probucol that is described in U.S. Pat. No. 5,262,439, for example, carboxylic acid esters and dicarboxylic acid esters and salts thereof; (ii) any monoester of probucol that has a greater solubility in water than probucol and which lowers plasma cholesterol, lowers LDL, and inhibits the expression of VCAM-1, as described in detail herein. In one embodiment, monoesters of probucol include dicarboxylic acid esters of probucol, including but not limited to the succinic acid, glutaric acid, adipic acid, suberic acid, sebacic acid, azelaic acid, and maleic acid esters. In another embodiment, the ester group includes a functional moiety which increases the solubility of the compound over probucol, including, but not limited to saturated and unsaturated dicarboxylic acids and salts thereof, amino carboxylic acids and salts thereof, aldehyde containing carboxylic acids and salts thereof, an amine group, a salt of an amine group, an amide group, aldehydes groups and the salts thereof. In yet another embodiment, the ester has a functional moiety selected from the group consisting of sulfonic acids, sulfonic acid esters, phosphoric acids, phosphoric acid esters, cyclic phosphates, polyhydroxyalkyl groups, carbohydrate group, C(O)-spacer-$SO_3H$, wherein spacer is —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S\text{-})$, —(aryl-O)—, —(O-aryl)—, —(alkyl-O)—, —(O-alkyl)—; n is 0, 1, 2, 3, 4, 5, 6, 7, 8, 9, or 10; C(O)-spacer-$SO_3M$, wherein M is a metal used to form a pharmaceutically acceptable salt, for example, sodium or potassium, C(O)-spacer-$PO_3H_2$, C(O)-spacer-$PO_3M_2$, C(O)-spacer-$PO_3HM$, C(O)-spacer-$PO_4H$, C(O)-spacer-$PO_4M$, $SO_3M$, —$PO_3H_2$, —$PO_3M_2$, —$PO_3HM$, cyclic phosphates, polyhydroxyalkyl, carbohydrate groups, C(O)-spacer-[O $(C_{1-3}\text{alkyl})_p]_n$, wherein n is as defined above and p is 1, 2, or 3, —[O($C_{1-3}$alkyl)$_p]_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

The term "pharmaceutically acceptable derivative" refers to a derivative of the active compound that upon administration to the recipient, is capable of providing directly or indirectly, the parent compound, or that exhibits activity itself.

The term "physiologically cleavable leaving group" refers to a moiety that can be cleaved in vivo from the molecule to which it is attached, and includes but is not limited to an organic or inorganic anion, a pharmaceutically acceptable cation, acyl (including but not limited to (alkyl)C(O), including acetyl, propionyl, and butyryl), alkyl, phosphate, sulfate and sulfonate.

Monoesters of probucol should be chosen for use in treating atherosclerosis and other cardiovascular and inflammatory diseases that have the proper lipophilicity to locate at the affected cite. The compound should not compartmentalize in low turnover regions such as fat deposits. In a preferred embodiment for treatment of cardiovascular disease, the pharmacokinetics of the compound should not be dramatically affected by congestive heart failure or renal insufficiency.

The active compound or a mixture of the compounds are administered in any appropriate manner, including but not limited to systemically, including orally or intravenously, or topically, including transdermally. A general range of dosage will be from 0.1 to 500 mg/kg body weight with a dose schedule ranging from once every other day to twice to several times a day. The length of dosing will range from a single dose given only once to twice daily dosages given over the course of two to six months.

In cardiovascular therapy, the compounds can also be administered directly to the vascular wall using perfusion balloon catheters following or in lieu of coronary or other arterial angioplasty. As an example, 2–5 mL of a physiologically acceptable solution that contains approximately 1 to 500 mM of the compound or mixture of compounds is administered at 1–5 atmospheres pressure. Thereafter, over the course of the next six months during the period of maximum risk of restenosis, the active compounds are administered through other appropriate routes and dose schedules.

Relatively short term treatments with the active compounds are used to cause the "shrinkage" of coronary artery disease lesions that cannot be treated either by angioplasty or surgery. A nonlimiting example of short term treatment is two to six months of a dosage ranging from 0.5 to 500 mg/kg body weight given at periods ranging from once every other day to three times daily.

Longer term treatments can be employed to prevent the development of advanced lesions in high-risk patients. A long term treatment can extend for years with dosages ranging from 0.5 to 500 mg/kg body weight administered at intervals ranging from once every other day to three times daily.

The active compounds can also be administered in the period immediately prior to and following coronary angioplasty as a means to reduce or eliminate the abnormal proliferative and inflammatory response that currently leads to clinically significant re-stenosis.

The active compounds can be administered in conjunction with other medications used in the treatment of cardiovascular disease, including platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, fenoprofen, mefenamic acid, flufenamic acid, sulindac. The compound can also be administered with corticosteriods.

MSE administered via subcutaneous implanted pellets (150 mg/kg/day time release pellets) blocks LPS-induced gene expression of VCAM-1 and MCP-1 in lungs in a mice model.

Oral administration of MSE (150 mg/kg/day) for six weeks lowers total plasma, ApO-B containing and HDL cholesterol levels in a New Zealand White rabbit model. The effects on plasma cholesterol are accompanied by marked inhibition of atherosclerosis lesion formation, macrophage accumulation and VCAM-1 expression.

Oral administration of MSE for two weeks selectively lowers apoB-containing lipoproteins in cholesterol-fed C57 black and apoE-knock out mice models without affecting HDL. Oral administration of MSE for two weeks in a hypercholesterolemic cynomolgous monkey model lowers total plasma and LDL cholesterol without effecting HDL.

MSE is not a mutagen in the bacterial Ames test. Oral administration of MSE at 1000/mg/kg/day for two weeks to rats did not result in any mortality and no effect on serum electrolyte and hematocrit values. Elevations in serum LDH, alkaline phosphatase, SGOT and SGPT were observed but were not statistically different from the untreated group and not accompanied with changes in liver morphology or histopathology.

For topical applications for the treatment of inflammatory skin disorders, the selected compound should be formulated to be absorbed by the skin in a sufficient amount to render a therapeutic effect to the afflicted site. The monoester of probucol must be physiologically acceptable. In general, compounds with a therapeutic index of at least 2, and preferably at least 5 or 10, are acceptable. The therapeutic index is defined as the $EC_{50}/IC_{50}$, wherein $EC_{50}$ is the concentration of compound that inhibits the expression of VCAM-1 by 50% and $IC_{50}$ is the concentration of compound that is toxic to 50% of the target cells. Cellular toxicity can be measured by direct cell counts, trypan blue exclusion, or various metabolic activity studies such as 3H-thymidine incorporation, as known to those skilled in the art.

The invention is further illustrated in the Examples below, which use MSE as a model compound. This is for illustration only, and not intended to limit the scope of the invention. Any other monoester of probucol as defined herein can be used to treat cardiovascular disease and inflammatory disorders in a substantially similar manner.

EXAMPLE 1

VCAM-1 Expression in Human Aortic Endothelial Cells

FIG. 1 is a bar chart graph of the comparison of the effect of the monosuccinic acid ester of probucol with probucol at 2.5 $\mu$M, 5 $\mu$M, 10 $\mu$M and 100 $\mu$M on VCAM-1 expression in human aortic endothelial cells in vitro as a percentage of VCAM-1 expression induced by TNF alone. The cells were incubated for sixteen hours in cell culture media at 37 degrees Celcius in a tissue culture incubator. After sixteen hours, the cells were washed, and incubated with antibodies to VCAM-1. The amount of antibody binding to the cells was determined by a colorometric ELISA assay using a horseradish peroxidase conjugated antibody to the VCAM-1 antibody. As indicated, MSE inhibits the expression of VCAM-1 under these conditions while probucol does not have an appreciable effect on VCAM.

EXAMPLE 2

ICAM-1 Expression in Human Aortic Endothelial Cells

Figure 2:
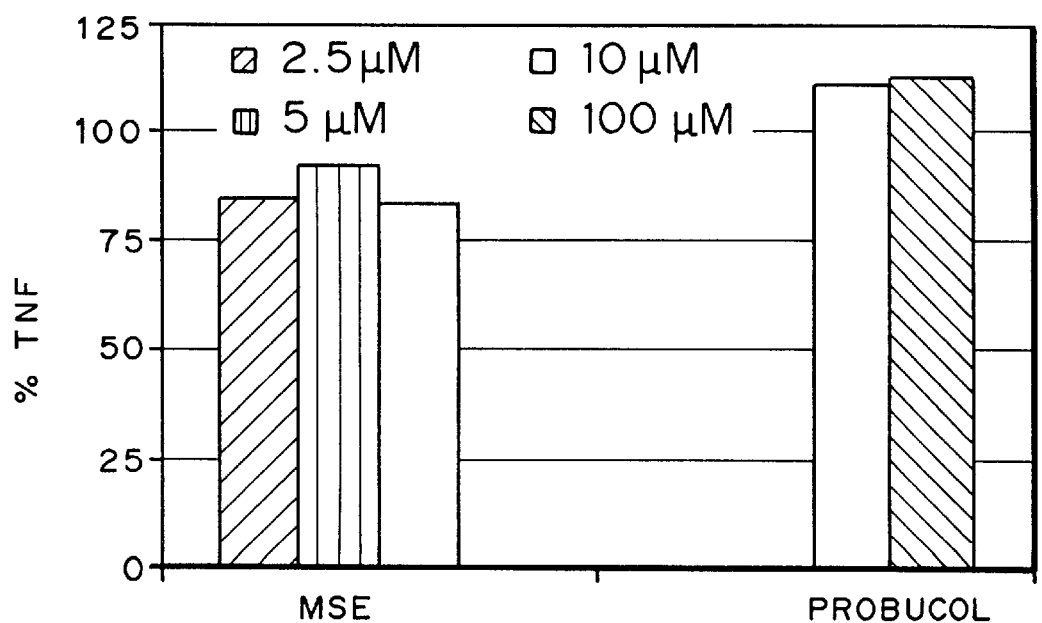
FIG. 2 is a bar chart graph of the comparison of the effect of the monosuccinic acid ester of probucol with probucol at 2.5 $\mu$M, 5 $\mu$M, 10 $\mu$M and 100 $\mu$M on ICAM-1 expression in HAEC cells.

FIG. 2 is a bar chart graph of the comparison of the effect of the monosuccinic acid ester of probucol with probucol at 2.5 $\mu$M, 5 $\mu$M, 10 $\mu$M and 100 $\mu$M on ICAM-1 expression in human aortic endothelial cells in vitro as a percentage of ICAM-1 expression induced by TNF alone. The cells were incubated for sixteen hours in cell culture media at 37 degrees Celcius in a tissue culture incubator. After sixteen hours, the cells were washed, and incubated with antibodies to ICAM-1. The amount of antibody binding to the cells was determined by a colorometric ELISA assay using a horseradish peroxidase conjugated antibody to the ICAM-1 antibody. As indicated, MSE had only a slight effect on ICAM expression which was not very concentration dependent, and probucol had no effect on ICAM expression.

EXAMPLE 3

MCP-1 Expression in Human Aortic Endothelial Cells

Figure 3:
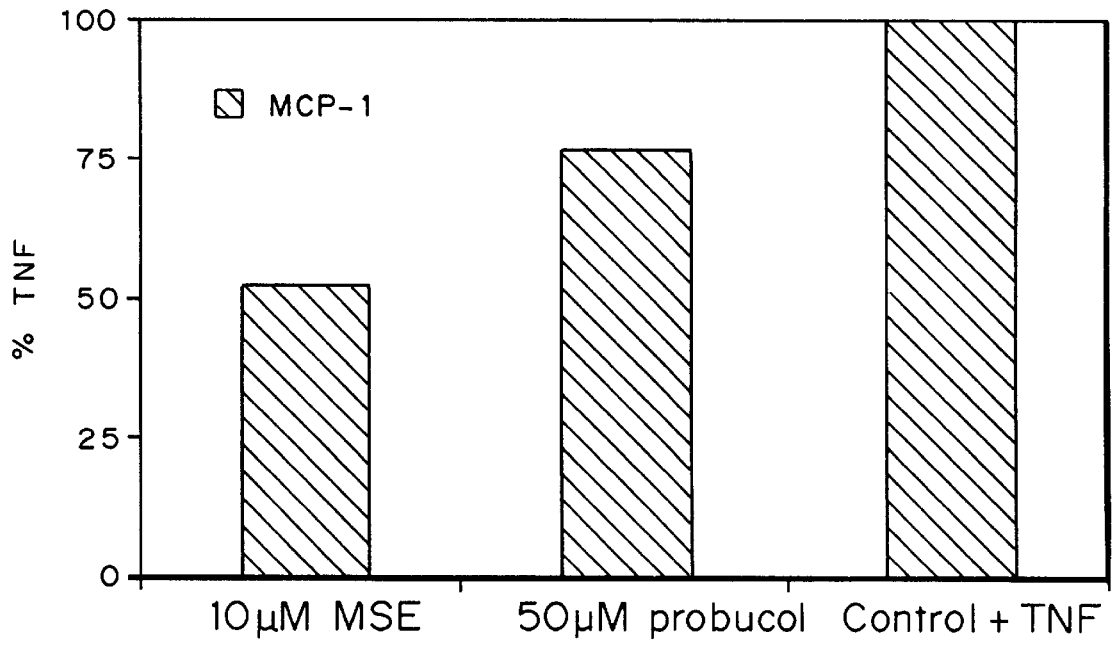
FIG. 3 is a bar chart graph of the comparison of 10 $\mu$M of the monosuccinic acid ester of probucol, 50 $\mu$M of probucol and TNF on MCP-1 expression in human aortic endothelial cells (HAEC).

FIG. 3 is a bar chart graph of the comparison of 10 $\mu$M of the monosuccinic acid ester of probucol, 50 $\mu$M of probucol and TNF on MCP-1 expression in human aortic endothelial cells cells (HAEC). The cells were treated with either TNF alone or together with 10 micromolar of the monosuccinic acid ester of probucol for four hours. The cell culture media was harvested and used to quantitate the amount of MCP-1 using a color-based ELISA assay. As illustrated, the monoester of probucol inhibited the expression of MCP-1 to a greater extent than probucol itself. MCP-1 is a chemoattractant protein that recruits monocytes to an atherosclerotic lesion.

EXAMPLE 4

Figure 4:
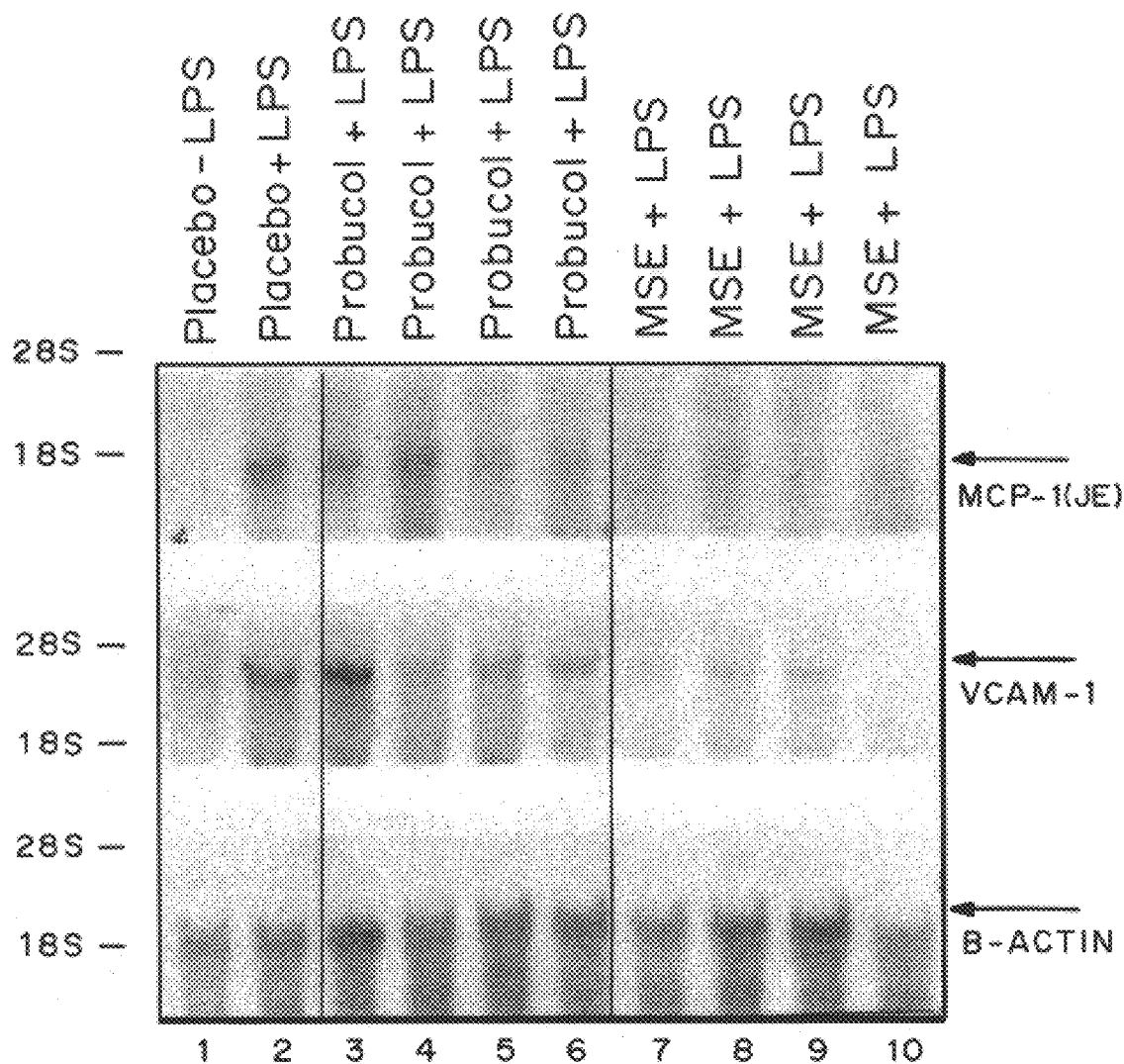
FIG. 4 illustrates the effect of the monosuccinic acid ester of probucol (10 and 25 $\mu$M), and probucol (50 $\mu$M) on gene expression in HAEC.
Figure 6:
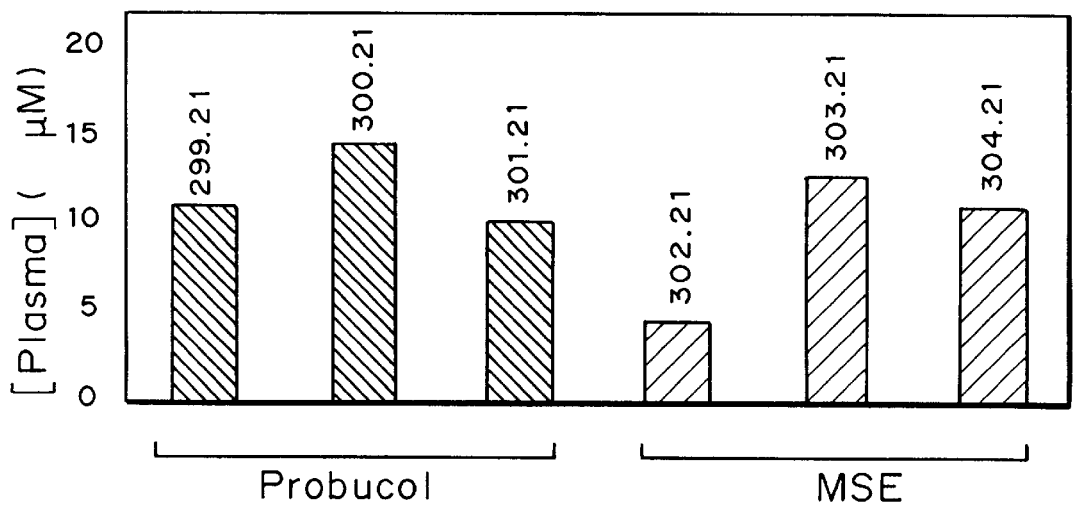
FIG. 6 is a bar chart graph of the comparison of the concentration of the monosuccinic acid ester of probucol and probucol in plasma of rabbits after three weeks of dosing.
Figure 7:
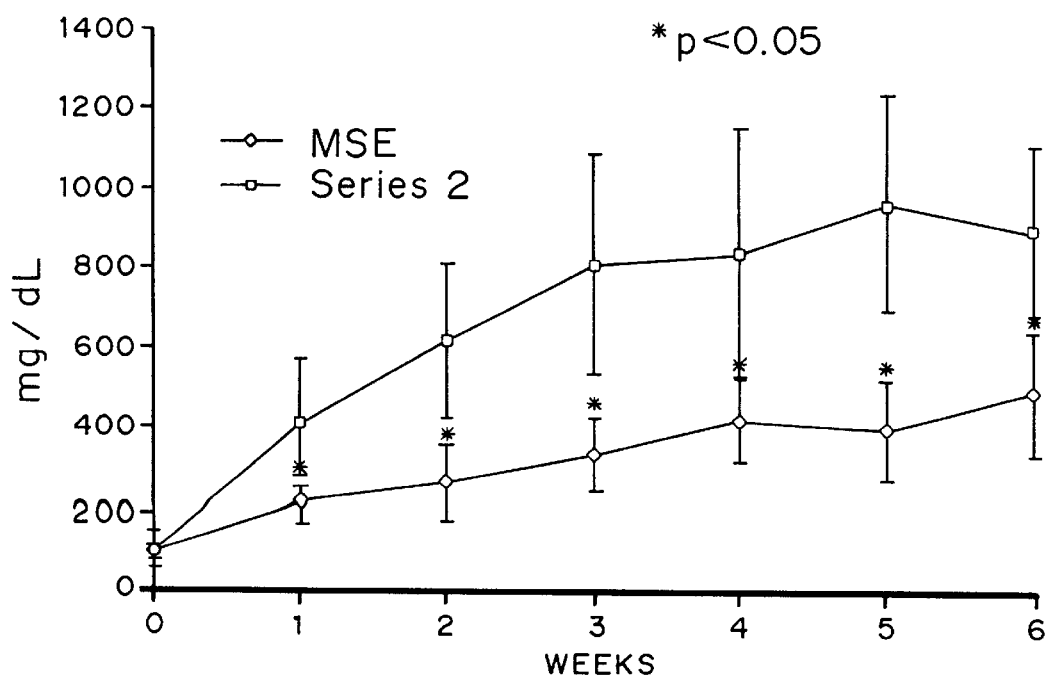
FIG. 7 is a graph of the effect of the monosuccinic acid ester of probucol on total serum cholesterol in the hypercholesterolemic rabbit model over six weeks.

Effect of Monosuccinic Acid Ester of Probucol on Gene Expression in Human Aortic Endothelial Cells in vitro FIG. 4 is a Northern blot analysis of VCAM-1 and MCP-1 gene expression from RNA isolated from the lungs of LPS-challenged ApoE knockout mice. Mice were administered MSE, probucol, and placebo subcutaneously in a 400 mg 90 day-time release pellet. After one week they were challenged intraperitoneally with 1 mg/kg of LPS. After two hours the animals were sacrificed and lungs frozen for RNA isolation. The RNA was size fractionated by denaturing 1.0% agarose gel electrophoresis, transferred to a nylon membrane and hybridized with a mouse JE-specific $^{32}$P-labelled cDNA probe. The membrane was subsequently stripped and hybridized with a mouse VCAM-1 specific cDNA and then a chicken β-actin specific cDNA probe.

EXAMPLE 5

Effect of Monosuccinic Acid Ester of Probucol on Cholesterol in Plasma of Lipid-fed Rabbits.

Figure 5:
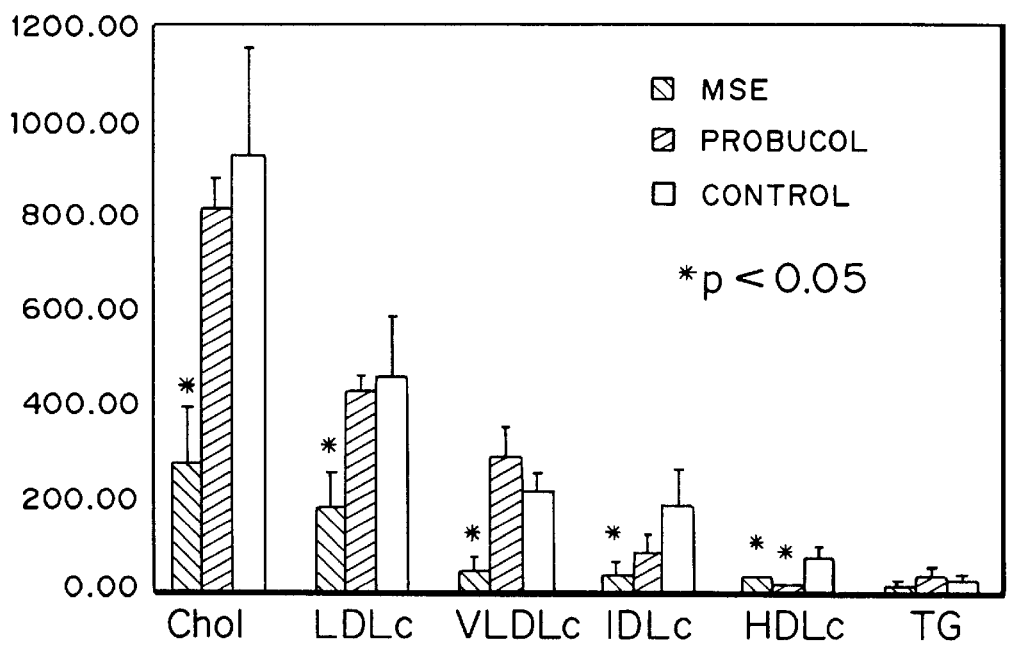
FIG. 5 is a bar chart graph of the effect of the monosuccinic acid ester of probucol and probucol on the cholesterol level in plasma of lipid-fed rabbits.

FIG. 5 is a bar chart graph of the effect of the monosuccinic acid ester of probucol and probucol on the total cholesterol and lipoprotein cholesterol levels in the plasma of lipid-fed rabbits. Rabbits were fed high-fat chow (0.5% cholesterol and 3% coconut oil) containing 0.5% wt/wt MSE or probucol for three weeks. Control animals were fed the same chow without drug added. Lipoprotein fractions were separated from whole plasma by fast phase liquid chromatography and analyzed for cholesterol content. MSE resulted in a statistically significant reduction in all lipoprotein fractions, and probucol only HDL cholesterol ($p<0.05$).

EXAMPLE 6

Comparison of Effect of MSE and Probucol Drug Level in Plasma of Rabbits Fed a High Cholesterol Diet for Three Weeks.

MSE or probucol were administered to rabbits in high-fat chow (0.5% cholesterol and 3% coconut oil) at a concentration of 0.5% wt/wt for three weeks. The drugs were extracted from plasma with ether and analyzed by high pressure liquid chromatography. As indicated, the level of probucol and MSE were similar, even though, as shown in the examples above, the compounds had a significantly different effect on the plasma cholesterol and lipoprotein levels.

EXAMPLE 7

Effect of MSE on NF-KB Activation

Human aortic endothelial cells were treated with TNF alone or in combination with 25 micromolar MSE or PDTC for a period of either one hour, two hours or four hours. The cells were washed and the nuclear extracts were prepared to perform gel shift analysis using a VCAM-1 promoter probe. It was determined that MSE does not affect NF-kB activation while PDTC does inhibit the activation of NF-kB.

EXAMPLE 8

Effect of MSE After Six Weeks on Cholesterol Level in Cholesterol Fed Rabbits

Figure 8:
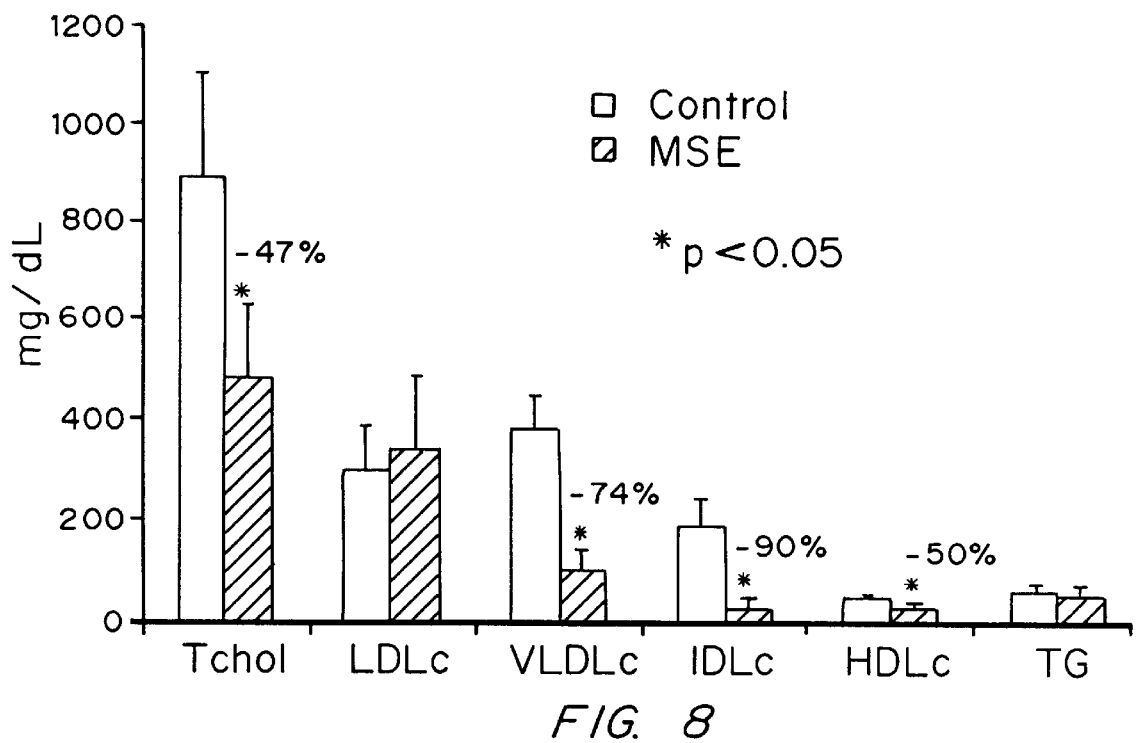
FIG. 8 is a bar chart graph of the effect of the monosuccinic acid ester of probucol on total cholesterol, LDLc, VLDLc, ILDLc, HDLc, and TG in lipid-fed rabbits after six weeks.

New Zealand white rabbits were fed high fat high cholesterol (0.5%) diets alone or together with 0.5 weight per weight (approximately 150 mg/kg/day) either AGE-3 or probucol for six weeks. FIG. 8 is a bar chart graph of the effect of the monosuccinic acid ester of probucol on total cholesterol, LDLc VLDLc, ILDLc, HDLc, and triglycerides (TG) in lipid-fed rabbits after six weeks. After six weeks, lipoprotein fractions were separated from whole plasma by fast phase liquid chromatography, and analyzed for cholesterol and triglyceride content. As indicated in Example 8, total cholesterol, as well as the cholesterol in VLDL and IDL were lowered more by treatment with AGE-3 than with probucol.

EXAMPLE 9

Effect of AGE-3 on Progression of Atherosclerosis in Hypercholesterolemic

Figure 9:
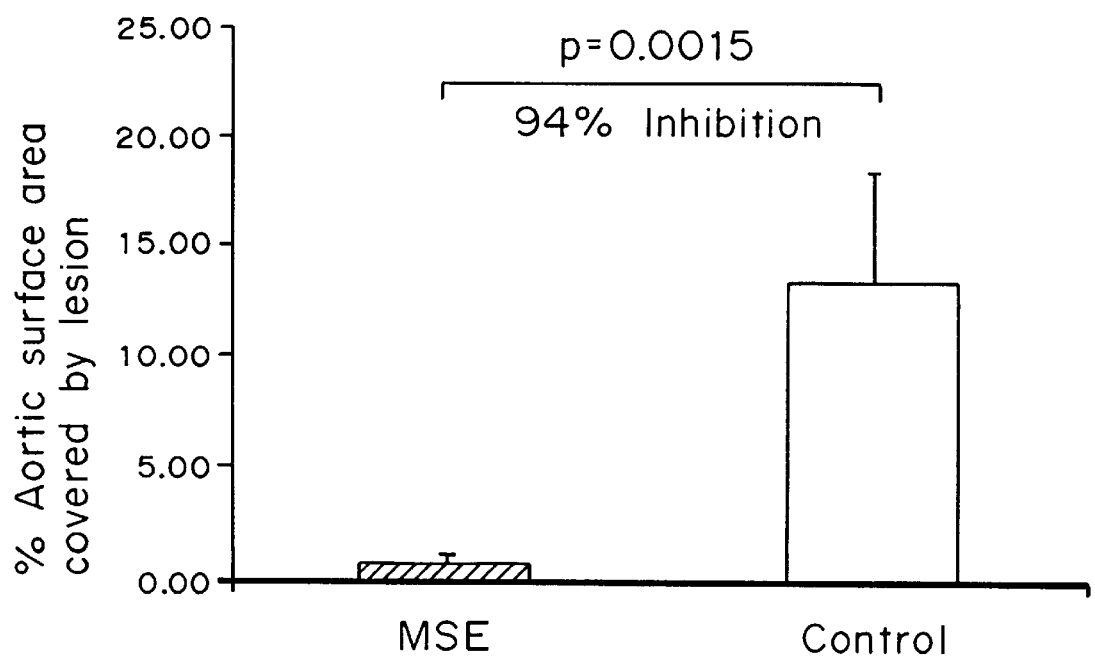
FIG. 9 is a graph of the percent aortic surface area covered by lesions in untreated lipid-fed rabbits and those treated with the monosuccinic acid ester of probucol.

The rabbits described in Example 8 were sacrificed and aortas obtained. The aortas were stained with sudan-4 and the extent of staining analyzed. FIG. 9 is a graph of the percent aortic surface area covered by lesions in MSE treated and untreated lipid-fed rabbits. The aortas of the rabbits that received AGE-3 had much less staining, indicating decreased atherosclerosis in those treated with the monosuccinic acid ester of probucol.

Sections of the aortas were immunostained for VCAM-1 expression or macrophage accumulation using antibodies for VCAM-1 or Ram-11 antigen. AGE-3 treatment markedly reduced VCAM-1 expression and macrophage accumulation (i.e., approximately more than 75%). In a similar experiment, probucol at the same dose was much less effective (less than 25% reduction in VCAM-1 expression and macrophage accumulation).

EXAMPLE 10

AGE-3 Lowers LDL Reversibly in Hypercholesterolemic Monkeys

Cynomolgus monkeys were made hypercholesterolemic prior to AGE-3 dosing by feeding a high fat cholesterol diet. The monkeys were then dosed orally with AGE-3 (100 mg/kg/day) for two weeks. The percent serum LDL cholesterol decreased in a range from 4 to 60 percent in the monkeys over this time period. Administration of the drug was then terminated, and serum cholesterol checked on day 29. The cholesterol level returned to the pretreatment level and was maintained there.

EXAMPLE 10

Figure 10:
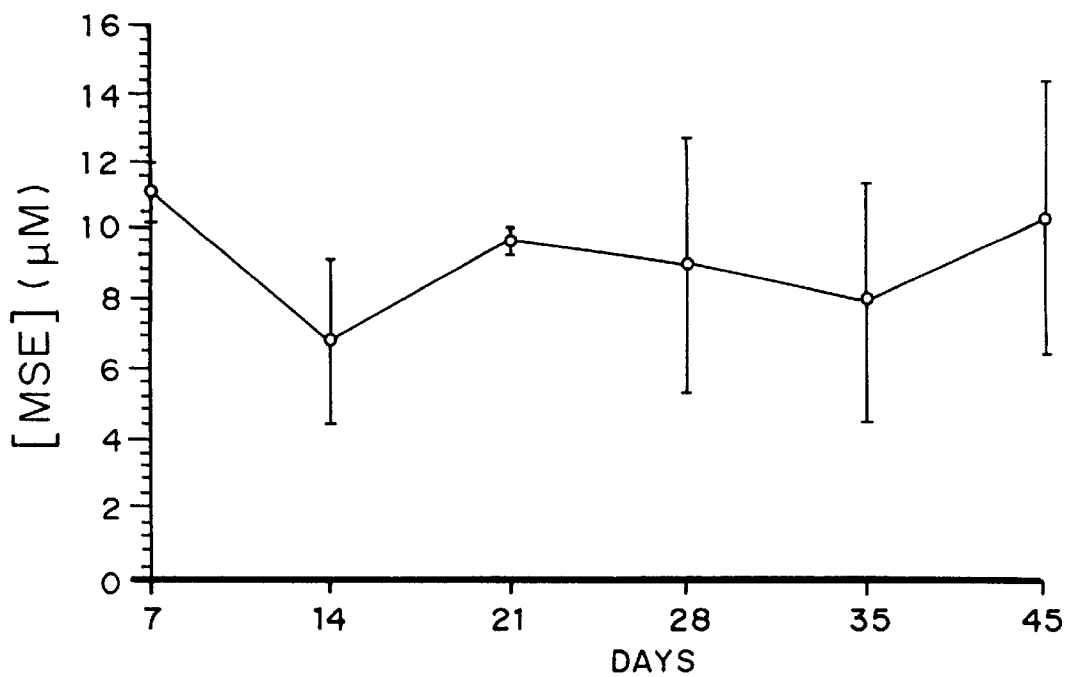
FIG. 10 is a graph of the plasma level of the monosuccinic acid ester of probucol in micromolar as a function of days of treatment.

FIG. 10 is a graph of the plasma level of the monosuccinic acid ester of probucol in micromolar as a function of days. As indicated, the plasmal level of MSE remained fairly constant.

EXAMPLE 11

Figure 11:
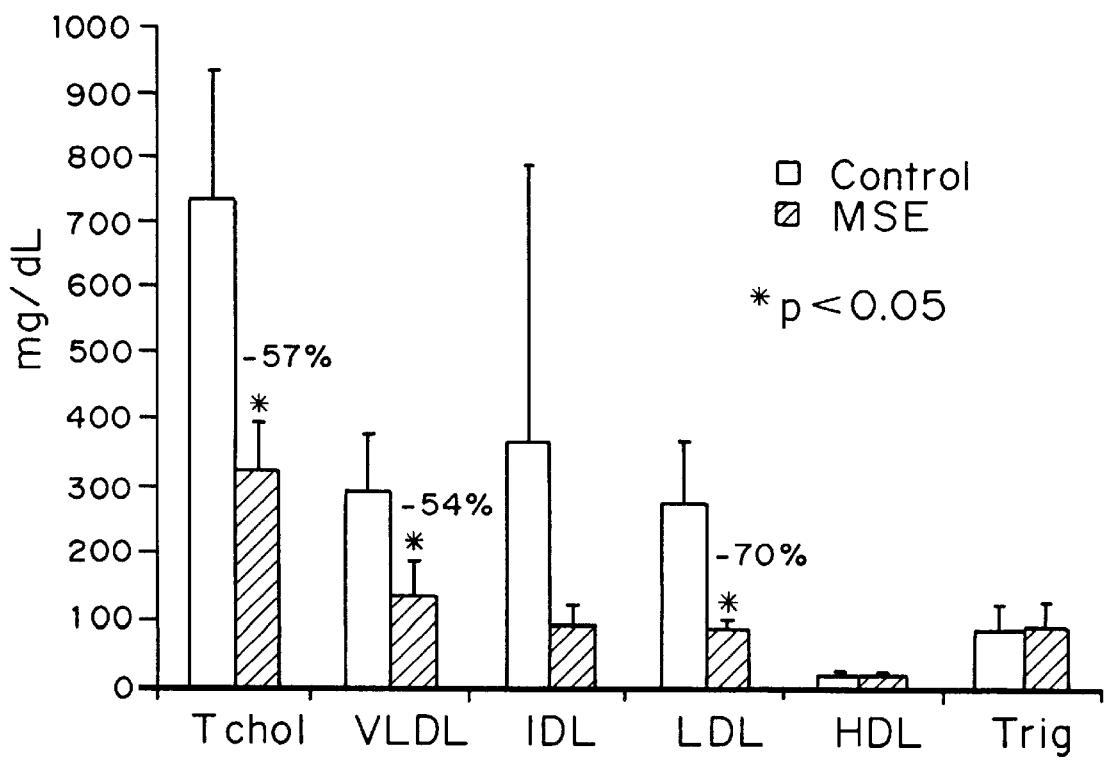
FIG. 11 is a bar chart graph of the total cholesterol, VLDL, IDL, LDL, HDL, and triglycerides in the ApoE-KO mouse two weeks after oral administration of the monosuccinic acid ester of probucol versus a control, in mg/ml.

FIG. 11 is a bar chart graph of the total cholesterol, VLDL, IDL, LDL, HDL, and triglycerides in the ApoE-KO mouse two weeks after oral administration of the monosuccinic acid ester of probucol (150 mg/kg/day) versus a control, in mg/ml.

EXAMPLE 12

Figure 12:
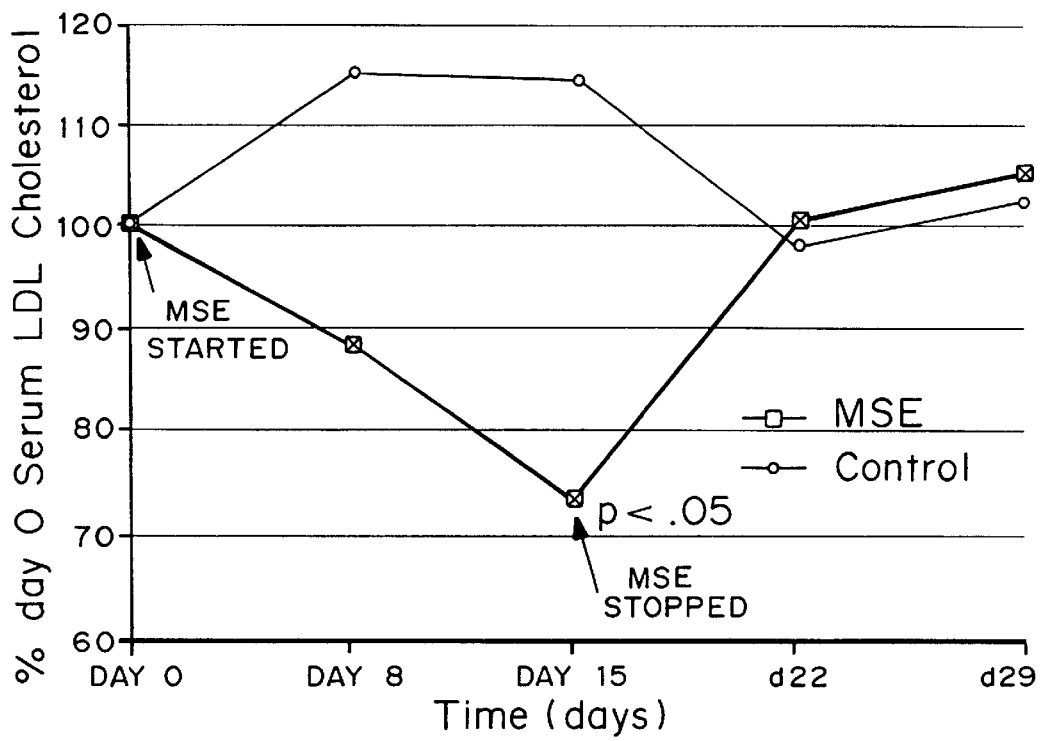
FIG. 12 is a graph of the serum level lowering of LDL in hypercholesterolemic monkeys over days during and after administration of the monosuccinic acid ester of probucol.

FIG. 12 is a graph of the reversible lowering of LDL in hypercholesterolemic monkeys over days during and after administration of the monosuccinic acid ester of probucol.

EXAMPLE 13

Figure 13:
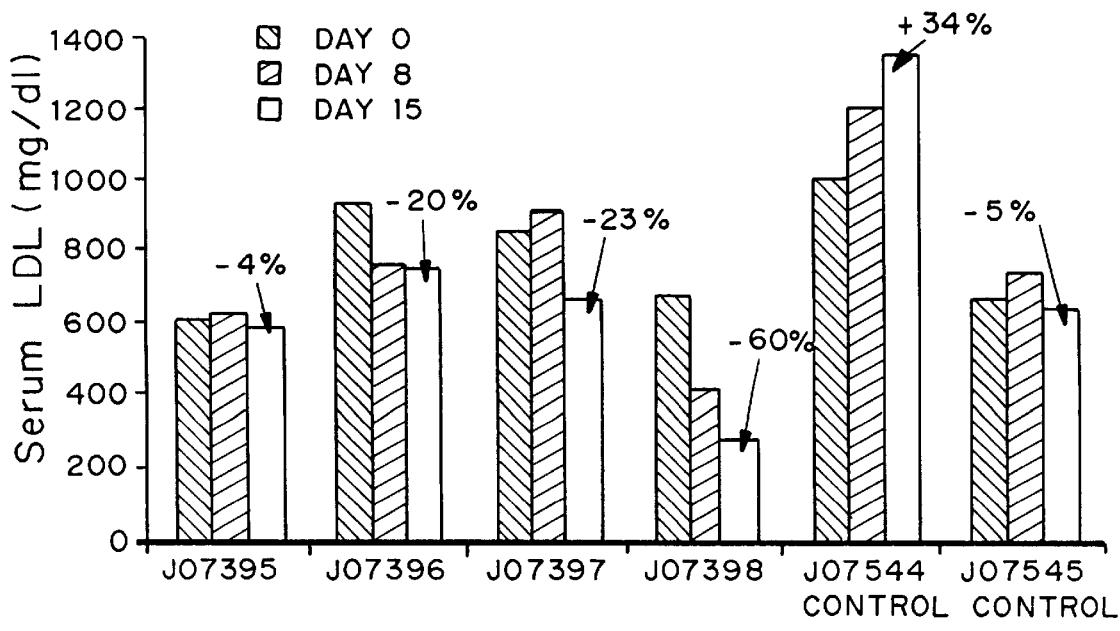
FIG. 13 is a bar chart graph of the effect of the monosuccinic acid ester of probucol on the serum LDL of hypercholesterolemic monkeys.

FIG. 13 is a bar chart graph of the effect of the monosuccinic acid ester of probucol on the serum LDL of hypercholesterolemic monkeys.

EXAMPLE 14

Figure 14:
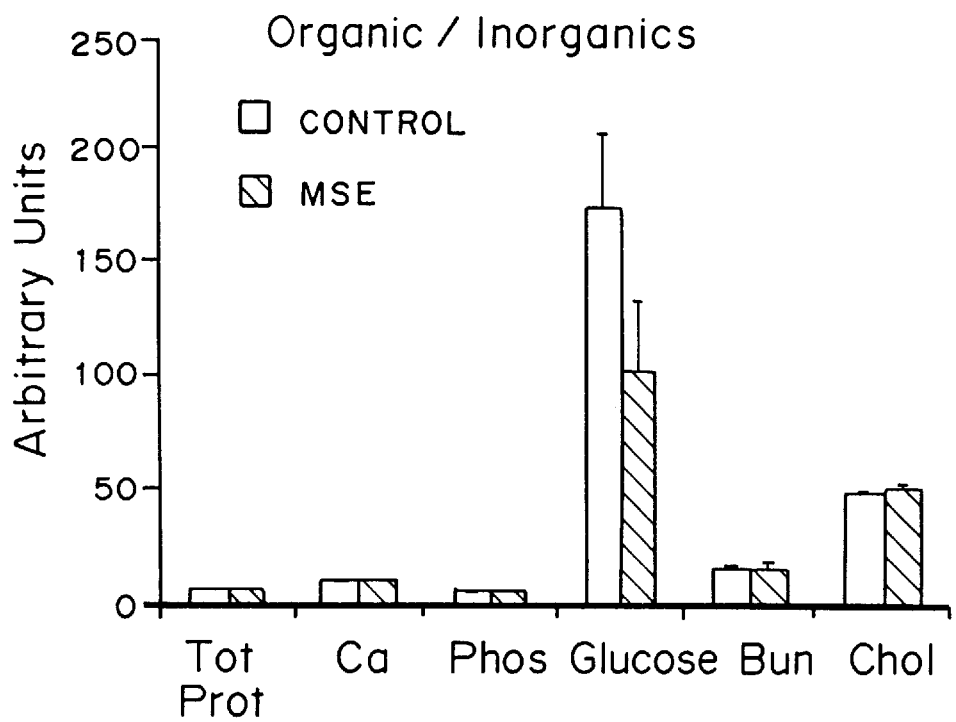
FIG. 14 is a bar chart graph of the effect in rats of two weeks of oral administration of the monosuccinic acid ester of probucol at 1000 mg/kg/d versus a control on total protein, calcium, phosphate, glucose, bun, and cholesterol, in arbitrary units.

FIG. 14 is a bar chart graph of the effect in rats of two weeks of oral administration of the monosuccinic acid ester of probucol at 1000 mg/kg/d versus a control on total protein, calcium, phosphate, glucose, bun, and cholesterol, in arbitrary units.

EXAMPLE 15

Figure 15:
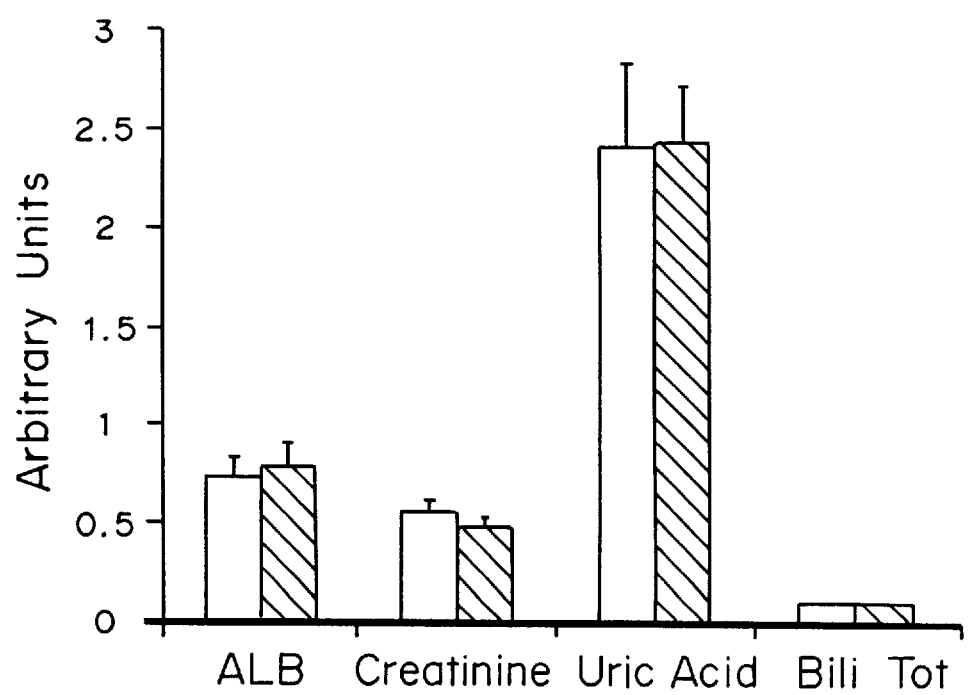
FIG. 15 is a bar chart graph of the effect in rats of two weeks of oral administration of the monosuccinic acid ester of probucol at 1000 mg/kg/d versus a control on albumin, creatinine, uric acid, and total bilirubin, in arbitrary units.

FIG. 15 is a bar chart graph of the effect in rats of two weeks of oral administration of the monosuccinic acid ester of probucol at 1000 mg/kg/d versus a control on albumin, creatinine, uric acid, and total bilirubin, in arbitrary units.

It has been noted that there is a difference in the effect of MSE and probucol in mice verses rabbits and monkeys in terms of the effect on total cholesterol and LDL. MSE is significantly more effective at reducing both cholesterol and LDL in rabbits and monkeys than in mice. MSE appears to have the same effect as probucol in mice, i.e., a minimal if any, effect on these two factors. MSE, however, inhibits the expression of VCAM-1 in all species tested.

III. Pharmaceutical Compositions

Humans, equine, canine, bovine and other animals, and in particular, mammals, suffering from any of the disease states described herein, including cardiovascular disorders, and inflammatory conditions mediated by VCAM-1, can be treated by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethylammonium, or ethylenediamine; or (c) combinations of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.1 to 500 mg/kg, preferably 1 to 100 mg/kg per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

For systemic administration, the compound is conveniently administered in any suitable unit dosage form, including but not limited to one containing 1 to 3000 mg, preferably 5 to 500 mg of active ingredient per unit dosage form. A oral dosage of 25–250 mg is usually convenient. The active ingredient should be administered to achieve peak plasma concentrations of the active compound of about 0.1 to 100 mM, preferably about 1–10 mM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be administered with other active materials that do not impair the desired action, or with materials that supplement the desired action, such as antibiotics, antifungals, antiinflammatories, or antiviral compounds. The active compounds can be administered with lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, aspirin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Suitable vehicles or carriers for topical application are known, and include lotions, suspensions, ointments, creams, gels, tinctures, sprays, powders, pastes, slow-release transdermal patches, aerosols for asthma, and suppositories for application to rectal, vaginal, nasal or oral mucosa.

Thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

The active compounds can be prepared with carriers that protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

If administered intravenously, preferred carriers are physiological saline or phosphate buffered saline (PBS).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221–229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Modifications and variations of the present invention will be obvious to those skilled in the art from the foregoing. All of these embodiments are considered to fall within the scope of this invention.

We claim:

1. A method for inhibition of VCAM-1 comprising administering to a patient an effective amount of a monoester of probucol or a pharmaceutically acceptable salt thereof.

2. The method of claim 1, wherein the monoester of probucol includes a functional moiety which increases the solubility of the compound over probucol.

3. The method of claim 2, wherein the functional moiety is selected from the group consisting of saturated and unsaturated dicarboxylic acids and salts thereof, amino carboxylic acids and salts thereof, and aldehyde containing carboxylic acids and salts thereof.

4. The method of claim 2, wherein the functional moiety is selected from the group consisting of an amine group, a salt of an amine group, an amide group, a salt of an amide group, an aldehyde group, a salt of an aldehyde group, sulfonic acids, sulfonic acid esters, phosphoric acids, phosphoric acid esters, cyclic phosphates, polyhydroxyalkyl groups, a carbohydrate group, C(O)-spacer-$SO_3H$, wherein spacer is —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S)$—, —(aryl-O)—, —(O-aryl)—, —(alkyl-O)—, —(O-alkyl)—; n is 0, 1, 2, 3, 4, 5, 6, 7, 8, 9, or 10; C(O)-spacer-$SO_3M$, wherein M is a metal used to form a pharmaceutically acceptable salt, C(O)-spacer-$PO_3H_2$, C(O)-spacer-$PO_3M_2$, C(O)-spacer-$PO_3HM$, C(O)-spacer-$PO_4H$, C(O)-spacer-$PO_4M$, $SO_3M$, —$PO_3H_2$, —$PO_3M_2$, —$PO_3HM_2$, cyclic phosphates, polyhydroxyalkyl, carbohydrate groups, C(O)-spacer-(O$(C_{1-3}$alkyl$)_p)_n$, wherein n is as defined above and p is 1, 2, or 3, —(O($C_{1-3}$alkyl$)_p)_n$, carboxy lower alkyl, lower alkyl-carbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

5. A method for the treatment of a disease mediated by VCAM-1 comprising administering to a patient an effective amount of a monoester of probucol or a pharmaceutically acceptable salt thereof.

6. The method of claim 5, wherein the disease is a cardiovascular disease.

7. The method of claim 6, wherein the cardiovascular disease is selected from the group consisting of atherosclerosis, post-angioplasty restenosis, coronary artery disease, angina, and small artery disease.

8. The method of claim 6, further comprising administering the monoester of probucol in combination with another cardiovascular agent selected from the group consisting of lipid lowering agent, platelet aggregation inhibitors, antithrombotic agents, calcium channel blockers, angiotensin converting enzyme (ACE) inhibitors and β-blockers.

9. The method of claim 5, wherein the disease is an inflammatory disease.

10. The method of claim 9, wherein the inflammatory disease is selected from the group consisting of rheumatoid arthritis, osteoarthritis, asthma, dermatitis, multiple sclerosis, and psoriasis.

11. The method of claim 9, further comprising administering the monoester of probucol in combination with another antiinflammatory agent.

12. The method of claim 5, wherein the monoester of probucol includes a functional moiety which increases the solubility of the compound over probucol.

13. The method of claim 12, wherein the functional moiety is selected from the group consisting of saturated and unsaturated dicarboxylic acids and salts thereof, amino carboxylic acids and salts thereof, and aldehyde containing carboxylic acids and salts thereof.

14. The method of claim 12, wherein the functional moiety is selected from the group consisting of an amine group, a salt of an amine group, an amide group, a salt of an amide group, an aldehyde group, a salt of an aldehyde group, sulfonic acids, sulfonic acid esters, phosphoric acids, phosphoric acid esters, cyclic phosphates, polyhydroxyalkyl groups, a carbohydrate group, C(O)-spacer-$SO_3H$, wherein spacer is —$(CH_2)_N$—, —$(CH_2)_n$—CO—, —$(CH_2)_n$—N—, —$(CH_2)_n$—O—, —$(CH2)_n$—S—, —$(CH_2O)$—, —$(OCH_2)$—, —$(SCH_2)$—, —$(CH_2S)$—, —(aryl-O)—, —(O-aryl)—, —(alkyl-O)—, —(O-alkyl)—; n is 0, 1, 2, 3, 4, 5, 6, 7, 8, 9, or 10; C(O)-spacer-$SO_3M$, wherein M is a metal used to form a pharmaceutically acceptable salt, C(O)-spacer-$PO_3H_2$, C(O)-spacer-$PO_3M_2$, C(O)-spacer-$PO_3HM$, C(O)-spacer-$PO_4H$, C(O)-spacer-$PO_4M$, $SO_3M$, —$PO_3H_2$, —$PO_3M_2$, —$PO_3HM$, cyclic phosphates, polyhydroxyalkyl, carbohydrate groups, C(O)-spacer-(O $(C_{1-3}alkyl)_p)_n$, wherein n is as defined above and p is 1, 2, or 3, —$(O(C_{1-3}alkyl)_p)_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

\* \* \* \* \*